US006610348B2

(12) United States Patent
Beyer et al.

(10) Patent No.: US 6,610,348 B2
(45) Date of Patent: Aug. 26, 2003

(54) GELLING AGENTS AND GELS CONTAINING THEM

(75) Inventors: Richard Beyer, Suva (FJ); Patrick J. Silcock, Dunedin (NZ)

(73) Assignee: Fonterra Tech Limited, Auckland (NZ)

( * ) Notice: Subject to any disclaimer, the term of this patent is extended or adjusted under 35 U.S.C. 154(b) by 0 days.

(21) Appl. No.: 09/987,320

(22) Filed: Nov. 14, 2001

(65) Prior Publication Data

US 2002/0058097 A1 May 16, 2002

Related U.S. Application Data

(63) Continuation of application No. 09/367,501, filed as application No. PCT/NZ98/00019 on Feb. 16, 1998, now abandoned.

(30) Foreign Application Priority Data

Feb. 17, 1997 (NZ) ................................. 314255

(51) Int. Cl.$^7$ ........................ A23J 3/10; A23L 1/0562
(52) U.S. Cl. ..................... 426/573; 426/34; 424/499; 424/403
(58) Field of Search ................... 426/34, 573; 424/499, 424/DIG. 10, 403

(56) References Cited

U.S. PATENT DOCUMENTS

| 3,137,631 A | | 6/1964 | Soloway |
| 3,406,119 A | | 10/1968 | Kosar et al. |
| 3,495,988 A | | 2/1970 | Balassa |
| 3,664,963 A | | 5/1972 | Pasin |
| 3,717,469 A | | 2/1973 | Slonimsky et al. |
| 3,932,680 A | | 1/1976 | Egli et al. |
| 4,055,555 A | | 10/1977 | Badertscher et al. |
| 4,159,982 A | * | 7/1979 | Hermansson ................ 530/360 |
| 4,217,369 A | | 8/1980 | Durst |
| 4,230,687 A | | 10/1980 | Sair et al. |
| 4,239,784 A | | 12/1980 | Guiraud et al. |
| 4,338,340 A | | 7/1982 | Morimoto et al. |
| 4,430,356 A | | 2/1984 | Ohyabu et al. |
| 4,656,041 A | | 4/1987 | Yagi et al. |
| 5,232,731 A | * | 8/1993 | Cain et al. .................... 426/580 |
| 5,252,352 A | | 10/1993 | Banach et al. |
| 5,358,730 A | * | 10/1994 | Dame-Cahagne et al. .. 426/573 |
| 5,368,871 A | * | 11/1994 | Konstance ................... 426/104 |
| 5,458,904 A | | 10/1995 | Zolper |
| 5,480,973 A | | 1/1996 | Goodlad et al. |
| 5,756,136 A | | 5/1998 | Black et al. |
| 5,866,189 A | | 2/1999 | Garwood et al. |
| 6,056,992 A | | 5/2000 | Lew |
| 6,187,367 B1 | * | 2/2001 | Cho et al. .................... 426/646 |

FOREIGN PATENT DOCUMENTS

| WO | 94/10854 | 5/1994 |
| WO | 98/18350 | 5/1998 |

OTHER PUBLICATIONS

Roefs et al, "Structure of Acid Casein Gels . . . ," Colloids and Surfaces, vol. 50, pp. 141–159 (1990).
Derwent Abstr. No. 91–105641; JP A 03–047042 (1991).
Derwent Abstr. No. 85–089475; JP A 60–037941 (1985).

* cited by examiner

Primary Examiner—Nina Bhat

(57) ABSTRACT

Described are modified casein gelling agents, gels and processes for preparing them. The modified casein gelling agent is casein in which the native structure has been disrupted.

24 Claims, No Drawings

GELLING AGENTS AND GELS CONTAINING THEM

This application is a continuation-in-part of Ser. No. 09/367,501 filed Nov. 29, 1999, abandoned, which is a 371 of PCT/NZ98/00019, filed Feb. 16, 1998, abandoned, which claims priority from New Zealand application Ser. No. 314,255, filed Feb. 17, 1997.

This invention relates to gelling agents, gels and to processes for preparing them. It also relates to products comprising the gels, in particular matrices for delivering active agent and food products.

BACKGROUND

Gels are formed from macromolecular hydrocolloids and have the ability to form non-deformable structures with low impact resistance. The classical gelling agent, which has been most widely studied, is gelatine. This is also the only known food grade hydrocolloid which is a protein. Gelatine is, nutritionally, a low quality protein and gels incorporating it have the disadvantages that they tend to harden on storage and may develop undesirable textural properties. Gelatine may also have negative religious and/or health connotations for some consumers, as it is produced in a manner destructive of animals and there may also be concerns arising from a perceived link with Transmissible Spongiform Encephalopathies such as Bovine Spongiforms Encephalopathy or Creutzfeld-Jacob Disease It is an object of the present invention to provide a gelling agent which will go some way towards overcoming the above disadvantages, or at least to provide the public with a useful choice.

SUMMARY OF THE INVENTION

In a first aspect the present invention may broadly be said to consist in a gelling agent which comprises modified casein, the native structure of the casein having been disrupted sufficiently to cause a composition to which the casein is added in use to gel.

Preferably, the gelling agent comprises a dispersion of modified casein in water and a suitable plasticiser, preferably glycerol.

In a further aspect the present invention provides a method of preparing a gelling agent which comprises the steps of:

(a) forming a dispersion comprising casein and water; and (b) heating the dispersion for a sufficient time and to a sufficient temperature to disrupt the native structure of the casein.

In another aspect the present invention may broadly be said to consist in a process of preparing a gelled product which comprises adding a gelling agent as defined above to a gellable composition.

In yet a further aspect the invention may broadly be said to consist in a process of preparing a gelled product which involves the use of casein as a gelling agent.

In still a further aspect the present invention may broadly be said to consist in a gelled product which includes a gelling agent as defined above.

In preferred embodiments, the gelled product is a food product.

In other alternative preferred embodiments, the gelled product is a delivery matrix which comprises (a) a matrix which includes the modified casein; and (b) an active agent incorporated in the matrix.

In yet a further aspect the present invention may broadly be said to consist in a method of preparing a gelled product which comprises the following steps:

(a) forming a dispersion comprising casein and water;

(b) heating the dispersion for a sufficient time and to a sufficient temperature to disrupt the native structure of the casein; and (c) removing the source of heat, adding other gellable components and allowing the resulting mixture to set into a gel.

Preferably, the dispersion also comprises a plasticiser (preferably glycerol) and a suitable buffer to maintain the pH in the range of about 6.1 to about 10.10.

DESCRIPTION OF THE INVENTION

As outlined above, the invention relates generally to gelled products and to macromolecular gelling agents used in their preparation.

The ability of a macromolecule to gel depends on interaction between molecules at restricted points along the macromolecule. Portions of the molecule that do not interact disperse in the continuous phase (usually water). Energy is usually required to disrupt the native structures of hydrocolloids. For instance, gelatine is manufactured by applying heat to collagen. The applicants have discovered that the native structure of casein can be disrupted sufficiently for gel formation. This can be achieved, for example, by heating, generally to a temperature of about 95–110° C. or above. It is this finding by the applicants which forms the basis for the present invention.

In a first aspect, the invention provides a gelling agent which comprises modified casein, in which the native structure of the casein has been disrupted sufficiently to cause a composition to which the casein is added to gel. The gelling agent preferably comprises a dispersion of the modified casein in a suitable plasticiser (preferably glycerol or glycerol combined with propylene glycol (1,2-propanediol) and water, although other forms of the modified casein are by no means excluded.

The gelling agents of the present invention have a number of potential applications. For example, in some embodiments of the invention, the gelling agents may be used in food products. In other embodiments the gelling agents may be used in preparing non-edible gels. For example, they may form part of a delivery matrix in which a matrix containing the modified casein encapsulates an active agent.

The preferred formulation of a particular gelling agent of the present invention will depend on the desired end use of the gel.

For example, alteration of the amount of plasticiser, if any present will change the characteristics of the resultant gel. Similar changes can be effected by changing the identity of the plasticiser. By way of illustration, using 1,2-propanediol as a plasticiser instead of, or partially instead of glycerol, results in a softer gel with a lower melting point. This may be desirable for some applications, for example where volatiles are to be entrapped or encapsulated by the gel matrix.

It is also possible to produce a lower melting point gel matrix through the addition of excess water during formation of the matrix. The excess water can then be removed again after the volatiles are encapsulated by gently drying over silica.

A still further approach to modifying the properties of the gel matrix is to replace a small amount of modified casein with gelatine (between 10% and 20%). This produces a lower melting point gel matrix which is softer than the equivalent matrix using casein alone.

Various embodiments of the invention are described in more detail below.

Food/Confectionery Applications

As noted above, in some preferred embodiments the gelling agents of the invention are used in preparing food products. In these embodiments, the gelling agents, and gelled products containing them, may be prepared by first forming a dispersion comprising water and preferably an edible plasticiser, most preferably glycerol, with the dispersion having a pH in the range of about 6.1 to about 8.0. It is preferred that the pH is about 7.5. It is generally desirable that the pH be within the above range when the gelling agent is to be incorporated into a food product, as the resulting gel may be waxy and brittle if the pH is lower than this, or may be unpalatable if the pH is above the upper limit of the range.

Suitable buffers to achieve this pH will be apparent to those skilled in the art. However, a preferred buffer is a combination of sodium citrate, calcium carbonate and sodium carbonate. It is preferred that the sodium citrate is present in an amount of about 1.0% to 2.0%, more preferably about 2.0%, by weight of the resulting gel, that the sodium carbonate is present in an amount of about 0.2% to 0.8%, more preferably about 0.4%, by weight of the gel, and that the calcium carbonate is present in an amount of about 0.4% to 1.0%, more preferably about 0.8% by weight of the gel.

It should also be noted that the calcium carbonate, as well as acting as a buffer, acts as a texture modifier, resulting in a gel with a firmer texture, which is desirable when the gel is to be used as a confectionery product such as a wine gum. The firmer texture is believed to result from interaction between the calcium ion and the casein.

In one preferred embodiment of the invention, glycerol is present in an amount of about 40% to about 55% by weight of the gelled product. Glycerol is a humectant and acts as a plasticiser in the gel. Thus, the more glycerol present, the softer the gel. The above range of glycerol concentrations has been found to be desirable for preparing gelled food products having a texture suitable for confectionery products such as wine gums. Of course, for other applications, a harder or softer gel may be desirable and the glycerol concentration should be adjusted accordingly.

The water acts to disperse the buffer. In the preferred embodiment of the invention mentioned above, in which the gelled product is suitable for use as a winegum type product, sufficient water is added so that water is present in an amount of about 26.7% to 34.6% by weight of the gel, more preferably about 30.2% by weight.

It is also preferred that the casein is washed before use in order to remove low molecular weight material. The presence of such low molecular weight material may result in the product having a bitter aftertaste. A suitable method of washing the casein is to use distilled water, preferably at a ratio of about 20:1 water:casein. The water and the casein are mixed together, and the mixture stirred for approximately one hour, the temperature then increased slowly to 30 C. and held for approximately 30 minutes. The mixture is then put on ice, stirred for a further two hours and the small molecular weight casein is removed by filtration, that is, it remains in the filtrate. Other suitable methods of washing the casein will be apparent to those skilled in the art.

The amount of water present significantly influences the texture of the gel—if too much water is added the resulting gel may be unacceptably soft for a particular application, whereas too little water will result in a gel which is too hard. Again, the amount of water added will need to be adjusted for the particular application to which the gelling agent is to be put.

The mixture of the buffer, glycerol and water is then preferably heated to about 40 C., and stirred until the buffer is dispersed. Once the buffer has been dispersed, casein is added to the mixture. The casein should be added sufficiently slowly to avoid the formation of lumps. In the preferred embodiment described above, the proportion of casein in the gel is about 18% by weight. Concentrations of casein significantly lower than this may produce gels which are too soft and fail to hold their shape after gelling, whereas significantly higher concentrations may produce gels which are too hard and do not have the 'gummy' texture required when the product is to be a confectionery product such as a wine gum. It will of course be appreciated that gels which are either soft or hard will be appropriate for applications other than as a confectionery such as a wine gum. Gels which contain more or less than 18% by weight of modified casein are therefore in no way excluded from the present invention.

It should be noted that, if, as is preferred, the casein is washed, the washed casein will retain a significant amount of water. This means that the water content of the casein will need to be determined and the amounts of water and casein adjusted accordingly, to give the desired proportions of water and casein in the composition.

After the casein has been added, the mixture should continue to be stirred. In addition, the mixture is heated to a sufficient temperature and for a sufficient time to disrupt the native structure of the casein sufficiently to allow gel formation to occur. It is preferred that the mixture be heated until the temperature reaches about 100 C., more preferably about 112 C., or when foaming lessens. The heating time required will depend on the rate of heating, but in practice, a heating time of between about 6 and 13 minutes will usually be sufficient.

The resulting solution, which is the gelling agent, is then removed from the heat. When the gelled product is to be a winegum-type confectionery, it is also preferred that additional components are then added to the solution. These preferred additional components are:

(1) a sweetening agent. A preferred sweetening agent is a combination of fructose and aspartame. However, alternative sweetening agents (both nutritive and non-nutritive) will be known to persons skilled in the art, and may also be used. A concentration of fructose of about 6.0% to about 10.0% by weight of the gel, most preferably about 8.0% by weight, and aspartame, in an amount of about 0.1% by weight of the gel have been found to produce an acceptable level of sweetness. However, the amounts of the sweetening agents may of course be adjusted depending on the desired level of sweetness in the gel.

(2) a flavor modifier which reduces bitterness. As the casein molecule suffers significant damage during heating, the resultant gel may have a bitter aftertaste. The use of a suitable flavor modifier will eliminate this. In the preferred embodiment, the flavor modifier is maltol (3-hydroxy-2-methyl-4-pyrone), present in an amount of about 0.1% by weight of the gel. Maltol minimizes bitterness and enhances sweetness.

(3) a texture modifier. A particularly preferred texture modifier which has been found to improve the texture of the gel is carrageenan, which is preferably added in an amount of about 0.15% to about 0.25% by weight of the gel. It will be appreciated by persons skilled in the art that alternative texture modifiers, for example gums such as carboxy methyl cellulose, may also be used.

Components (1) to (3) are stirred into the solution after it has been removed from the heat, until all components have been dispersed. If desired, food grade colorings and/or flavorings may then also be added.

The resulting mixture is then allowed to cool and set. It is preferred that the mixture be poured into a mould so that the gel sets in a desired shape. When the gelled product is to be a winegum-type confectionery, if desired, the gelled product can be coated with an agent which hardens the outside of the gel. If such a coating is desired, then approximately one hour after pouring, the gelled product can be removed from the mould and coated with the hardening agent. A preferred hardening agent is a citric acid/calcium citrate dip, consisting of an aqueous solution comprising about 15% by weight citric acid and 1% by weight calcium citrate. The pH of the dip is preferably about 2.0, which is lower than the isoelectric point of casein (pH 4.5).

EXAMPLE 1

| Component | Percentage (by weight) |
|---|---|
| Glycerol | 40.0 |
| Water | 10.7 |
| Washed casein | 37.1 |
| Fructose | 8.8 |
| Sodium citrate | 2.0 |
| Calcium carbonate | 0.8 |
| Sodium carbonate | 0.4 |
| Carrageenan | 0.2 |
| Flavour | 0.2 |
| Maltol | 0.1 |
| Aspartame | 0.1 |
| Colour | 0.003 |
| Dip | |
| Water | 74.0 |
| Citric acid | 15.0 |

Method (1) Casein and distilled water were stirred for one hour at a 20:1 ratio water:casein. The temperature was increased slowly to 30 C. and held for 30 minutes. The sample was then put on ice and stirred for a further 2 hours and filtered. A moisture determination of the casein indicated an average moisture content of 63.4% and the above formulation was calculated to provide a final moisture content of 30.2% and a casein content of 18.0%.

(2) The sodium citrate, sodium carbonate and calcium carbonate were added to the glycerol and water. The mixture was heated to 40 C. and stirred until dispersed.

(3) The washed casein was added slowly to avoid the formation of lumps.

(4) Stirring was continued and the mixture was heated until the temperature reached 110 C. to 112 C. or until foaming stopped.

(5) The mixture was removed from the heat and the following were stirred in until all dispersed: carrageenan, fructose, maltol and aspartame. The colour and flavour were then added.

(6) The mixture was poured into a mould and left for one hour. The gel was removed from the mould and placed in a citric acid/calcium citrate dip for ten minutes.

The resulting gelled product had a texture and flavour suitable for use as a winegum type confectionery product.

Non-food Applications

As noted above, the gelling agents of the present invention may also be used in products other than food products, for example as part of a delivery matrix. In such products, a matrix comprising the modified casein encapsulates an active agent for which a slow or controlled release from the composition is desired.

The delivery matrices comprising the gelling agents of the present invention may conveniently be prepared by first preparing a modified casein matrix, melting the matrix, adding the active agent and any other desired ingredients (such as an emulsifier if required), and then allowing the mixture to cool and set into a desired shape.

The modified casein matrix may generally be prepared by heating casein in the presence of water and preferably a plasticiser, and at a pH of about 6.1 to about 10.10. It is preferred that the heating be carried out under basic conditions, and preferably at a pH of about 9.7. One preferred buffer which may be used to achieve the desired pH is sodium carbonate, but other buffers, such as potassium carbonate, trisodium phosphate and calcium hydroxide may also be used.

It is preferred that the plasticiser used is glycerol, but other plasticisers, such as sorbitol, may also be used and are by no means excluded from the invention.

It is also generally preferred that the casein be heated in the presence of a cross-linking agent such as dimethyl adipate. The use of a cross-linking agent increases the molecular weight of the modified casein and also decreases its solubility, resulting in a firmer gel. These properties are generally desirable when the gelling agents of the invention are to be used in delivery matrices.

The preferred method of preparation is to dissolve the buffer in water, add the plasticiser and the cross-linking agent, and heat the mixture to 50 C. before adding the casein. Once the casein is added, the mixture is heated further, preferably to around 130 C., and continued until the casein is cross-linked sufficiently to reduce solubility. Following the heating, the mixture is allowed to cool and set into a desired shape. An active agent can then be incorporated into the matrix, with the aid of an emulsifier if required, by melting the matrix together with the emulsifier (preferably at a temperature of around 70 C.–80 C.) and mixing in the active agent until homogeneity is achieved. An example of a suitable emulsifier is a mixture of 80% Datem (mono- and diglyceride monoacetyl and diacetyl tartaric acid)/20% Calcium phosphate, although other suitable emulsifiers will be apparent to those skilled in the art. The mixture may then be moulded into the desired shape.

It will be appreciated that the active agent can be any substance which it is desired to incorporate in a delivery matrix. For example, the active agent could be a pharmaceutical. Alternatively, it could be an insect or animal attractant or repellant, as in the examples which follow.

The relative amounts of the components used in preparing the modified casein matrix will again depend on the end use to which the gelled product is to be put. However, when the gelled product is to be a delivery matrix incorporating an active agent such as an animal attractant or repellent, an example of a suitable matrix formulation is as follows: about 34% glycerol, about 32.6% lactic acid casein, about 21.7% water, about 6.5% sodium carbonate and about 5.2% dimethyl adipate.

The relative proportions of the modified casein matrix, active agent and emulsifier in the final gelled product will also depend on the nature of the active agent and the end use to which the product is to be put. Generally, it has been found that active agent can be incorporated satisfactorily into the modified casein matrix at a weight ratio of up to about 1:10 active agent:modified casein matrix. For example, a suitable composition may comprise around 5% by weight active agent, 1% emulsifier and 94% modified casein matrix. Emulsification difficulties may be experienced if the concentration of active agent is much higher, for example around 20% by weight.

It should be noted that, especially when relatively chemically reactive active agents are being used, it may also be desirable to decrease the pH of the modified casein matrix to a more neutral level, to minimize the risk of the active agent undergoing chemical modification as a result of the relatively high pH of the modified casein matrix. Glucono-d-lactone is the preferred acid for achieving the decrease in pH because of its low solubility and because it brings about a slow decrease in pH. However, other weak organic acids such as citric acid may also be used; these would have the advantage of being less expensive than glucono-d-lactone.

EXAMPLE 2

Entrapped Crayfish Attractant

| Matrix Formulation | |
|---|---|
| Component | % (w/w) |
| Glycerol | 34.0 |
| Lactic Acid Casein | 32.6 |
| Water | 21.7 |
| Sodium carbonate | 6.5 |
| Dimethyl adipate | 5.2 |

Method of Preparation of Matrix

The sodium carbonate was dissolved in the water; glycerol and dimethyl adipate were added and stirred. The mixture was heated to 50 C., the casein added and heating continued to 130 C. The mixture was poured onto a board, flattened and left to cool.

The cray attractant was incorporated into the matrix with the aid of an emulsifier in the proportions outlined below:

| Component | % (w/w) |
|---|---|
| Matrix | 94.0 |
| Emulsifier (80% Datem/20% Ca$_3$PO$_4$) | 1.0 |
| Cray attractant | 4.0 |

The attractant was occluded using the following method:
The matrix was cut into small pieces and heated with the emulsifier in a crucible in a water bath. The mass was heated until the matrix had melted (temperature between 70° C. and 80° C.). The mass was mixed until homogeneous. The mass was removed from the heat and the attractant was weighed directly into the mass and mixed until a homogeneous, with extra heating to facilitate mixing. The mass was removed from the crucible and moulded into the desired shape.

Further compositions were prepared, varying the proportion of cray attractant (20%, 10% and 1% attractant). These formulations were prepared using the same method as described above but with the following modification: the cray attractant was weighed onto a small piece of paraffin film (<0.01 g) then added to the matrix without requiring removal of the matrix from the heat,. These formulations were as follows:

| | Formulation (weight in grams) | | |
|---|---|---|---|
| Component | 1 | 2 | 3 |
| Matrix | 19.5 | 22.0 | 24.25 |
| Emulsifier (80% Datem/20% Ca$_3$PO$_4$) | 0.5 | 0.5 | 0.5 |
| Cray attractant | 5.0 | 2.5 | 0.25 |

Three further formulations incorporating the cray attractant were prepared, but having a pH of about 6, 7 and 8 respectively. These formulations were prepared using the same method described above (for formulations 1 to 3) but with the modification that glucono-d-lactone was added at the same time as the cray attractant. These formulations were as follows:

| | Formulation (weight in grams) | | |
|---|---|---|---|
| Component | 4 | 5 | 6 |
| Matrix | 22.0 | 22.0 | 22.0 |
| Emulsifier (80% Datem/20% Ca$_3$PO$_4$) | 0.5 | 0.5 | 0.5 |
| Cray attractant | 2.5 | 2.5 | 2.5 |
| Glucono-d-lactone | 2.57 | 3.06 | 3.37 |
| pH (approximate) | 8 | 7 | 6 |

It was noted that the practice of weighing the attractant onto a small piece of paraffin film and adding it directly to the molten matrix, as opposed to removing the matrix from the heat and weighing the extract directly into the mass, resulting in the sample produced being more homogeneous, more cohesive and less honey comb like.

The resulting composition can be used to attract crayfish by placing the composition in craypots. It is believed the attractant will release slowly from the composition and will therefore have the advantage of lasting for a considerable time, generally around two days.

EXAMPLE 3

Entrapped Tom Cat Pheromone

A composition containing entrapped tom cat pheromone was prepared, having the following formulation:

| Component | Weight (g) | % (w/w) |
|---|---|---|
| Casein matrix | 21.25 | 86.91 |
| Vegetable oil | 2.00 | 8.18 |
| Acetone | 1.00 | 4.09 |
| Tom cat pheromone | 0.20 | 0.82 |

Method of Preparation

The casein matrix was prepared using the same method as described above in Example 2.

The tom cat pheromone was dispersed in the acetone and then blended with the vegetable oil. The casein matrix was melted and the tom cat pheromone, acetone and vegetable oil were added and mixed until homogeneous. The base was then moulded into the desired shape.

The resulting composition is believed to release tom cat pheromone at a slow rate. Without wishing to be bound by any theory, it is believed the active ingredient will diffuse through the casein matrix and volatilise. As herbivores are believed to be repelled by the scent of carnivore pheromones, it is envisaged that the composition has potential utility in repelling herbivores. For example, discs of the composition can be attached to trees (eg pine seedlings) which require protection from herbivores such as possums.

EXAMPLE 4

Entrapped Mink Anal Gland Pheromone

A composition in the form of discs incorporating mink anal gland pheromone (3,3-dimethyl-1,2-dithiolane (DMDT)) was prepared, using the method described above in Example 2 (entrapped cray attractant).

The formulation for the composition was as follows:

| Component | % (w/w) |
| --- | --- |
| Casein matrix | 90.8 |
| (80% Datem/20% $Ca_3PO_4$) | 2.0 |
| DMDT | 7.2 |

Water was added at a ratio of 1:5 water to casein matrix, to aid the melting of the casein matrix. The excess water was removed from the finished discs by drying over silica gel at room temperature.

DMDT is a carnivore odor which appears to induce a fear response in possums. The compositions containing entrapped DMDT are therefore believed to be potentially useful as a repellent for herbivores. In particular, they may be attached to pine seedlings in order to repel possums from the seedlings.

EXAMPLE 5

Entrapped Stoat Anal Gland Attractant

Male and female stoat anal gland extracts were incorporated into the casein matrix at a rate of 1%. To lower the melting point of the casein matrix the formulation was altered to include gelatine. The modified casein matrix formulation is as follows:

| Component | % (weight/weight) |
| --- | --- |
| glycerol | 34.0 |
| casein | 27.7 |
| water | 21.9 |
| sodium carbonate | 6.5 |
| dimethlyadipate | 5.0 |
| gelatine | 4.9 |

The composition of the finished products were as follows:

| Component | % (weight/weight) |
| --- | --- |
| casein matrix | 97.0 |
| emulsifier (80% Datem/20% $Ca_3PO_4$) | 2.0 |
| male stoat anal gland extract | 1.0 |
| casein matrix | 97.0 |
| emulsifier (80% Datem/20% $Ca_3PO_4$) | 2.0 |
| female stoat anal gland extract | 1.0 |

Water was added at a ratio of 1:5 water to casein, to aid the melting of the casein matrix. The casein matrix and emulsifier were melted at 55° C., mixed until visually homogenous, the temperature was adjusted to 50° C., the extract added and gently mixed. The mass was then cut to the desirable shape and cooled. The excess water was removed from the finished squares by drying over silica gel.

EXAMPLE 6

Entrapped Rat Repellent

Two repellents were occluded in a casein matrix. The two chemicals were 3-(S-methyl)-3-methylbutan-1-ol and 3-isopentenyl methyl sulphide.

The casein matrix used for the rat repellents was the same as that used for the stoat anal glands.

The composition of the finished products were as follows:

| Component | % (weight/weight) |
| --- | --- |
| casein matrix | 93.0 |
| emulsifier (80% Datem/20% $Ca_3PO_4$) | 2.0 |
| 3-(S-methyl)-3-methylbutan-1-ol | 5.0 |
| casein matrix | 93.0 |
| emulsifier (80% Datem/20% $Ca_3PO_4$) | 2.0 |
| 3-isopentenyl methyl sulphide | 5.0 |

Water was added at a ratio of 1:5 water to casein, to aid the melting of the casein matrix. The casein matrix and emulsifier were melted at 55° C., mixed until visually homogenous, the temperature was adjusted to 50° C., the extract added and gently mixed. The mass was then cut to the desired shape and cooled. The excess water was removed from the finished squares by drying over silica gel.

EXAMPLE 7

Entrapped Fly Attractant

A fly attractant was incorporated into two matrices: a solid gel matrix (as above), and a thick paste-like matrix.

A. Gel Product

The product was prepared as per the stoat product with the exception the attractant was added at 2% and 10%.

The composition of the products were as follows:

| Component | % (weight/weight) |
| --- | --- |
| casein matrix | 96.0 |
| emulsifier (80% Datem/20% $Ca_3PO_4$) | 2.0 |
| Fly attractant | 2.0 |
| casein matrix | 88.0 |
| emulsifier (80% Datem/20% $Ca_3PO_4$) | 2.0 |
| Fly attractant | 10.0 |

The product was prepared as per the stoat product with one exception. Sodium sulfide was dispersed in the extra water (added to aid melting at a rate of 1.5% (w/w) of the fly attractant.

Due to the highly volatile nature of the fly attractant components losses in the manufacturing process were believed to be in the range of 50%. These products successfully attracted flies into traps in a field trial conducted in North Taranaki for a minimum of four weeks.

B. Paste Product

To minimize the high losses of fly attractant associated with the above product, the casein matrix was reformulated to produce a paste-type product at room temperature (it gels at low temperatures).

The modified formulation is as follows:

| Component | % (weight/weight) |
|---|---|
| Plasticiser (propylene glycol) | 42.3 |
| casein | 18.5 |
| water | 22.9 |
| maltodextrin (DE 10) | 11.0 |
| thin boiling starch (TB840) | 3.7 |
| sodium carbonate | 1.0 |
| calcium carbonate | 0.5 |
| xanthan gum | 0.1 |

The casein paste is prepared by the following procedure:

The water and propylene glycol are mixed;

The casein, thin boiling starch (TB840), sodium carbonate, calcium carbonate and xanthan gum are dry blended (powdered mix);

The powdered mix is dispersed in the water and propylene glycol and mixed until free of lumps;

The mixture is heated to between 95° C. and 100° C. for 10 minutes;

The maltodextrin (DE 10) is added and mixed until dispersed;

The hot mass is cooled to room temperature.

A fly attractant can be prepared from the above product by the following method:

The casein paste matrix is warmed to between 25° C. and 30° C.;

the emulsifier and sodium sulphide dispersed in the matrix;

the attractant added and mixed until dispersed.

At this stage the mass can either packed off directly into a suitable tube or heated to 35° C. (to facilitate filling) then packed off into a suitable tube.

| Component | % (weight/weight) |
|---|---|
| casein paste matrix | 92.925 |
| emulsifier (80% Datem/20% Ca$_3$PO$_4$) | 2.000 |
| Fly attractant | 5.000 |
| sodium sulphide | 0.075 |

The texture/viscosity of the product can be easily altered, for example by:

1) Substituting propylene glycol for glycerol will increase the firmness of the final product.

2) Altering the ratio of maltodextrin to thin boiling starch. As the proportion of thin boiling starch is increased the firmness of the product is increased, alternatively increasing the proportion of maltodextrin softens the product.

EXAMPLE 8

The gelling gents produced by the invention are clear, meltable winegum-like products. This is demonstrated by the following example. Casein gel is prepared as in Example 1 but without an acid dip. The gels were clear/translucent elastic and rubbery wine gum-like confectionery products that possessed a clean flavor. Samples of gels were filled into four 20 mL Scintillation vials. The vials were incubated at 40° C., 50° C., 60° C. and 70° C. for 30 minutes. After 30 minutes the gels were examined and any changes in appearance noted. At 40° C., the gel started to soften but held its shape. At 50° C., the gel could be shaped but did not flow. At 60° C., the gel had softened further but had not melted. At 70° C., the gel liquefied and could be poured. It was a viscous solution with excellent clarity.

The experiment was repeated with a gelatine-based wine gum though an additional sample had to be run at 85° C. At 40° C., the gel started to soften but held its shape. At 50° C., the gel softened further but still held its shape. At 60° C., the gel could be shaped but did not flow. At 70° C., the gel was similar to that at 60° C. At 85° C., the wine gum liquefied and formed a clear viscous solution.

It is believed that the novel gelling agents and gels according to the present invention will find widespread acceptance. For example, they are suitable for use in food products such as confectionery, as described above. It is believed that the gelled products according to the invention will possess enhanced textural properties on storage as compared with currently available gels formed from gelatine.

In other applications, the gelling agents may be employed in the preparation of non-edible gels. Such gels may for example form part of a delivery matrix, as described above. Pharmaceutical/medical applications are also possible.

Those persons skilled in the art will appreciate that the above description is exemplary only and that variations and modifications are possible without departing from the scope of the invention.

What we claim is:

1. A gelling agent which comprises a plasticizer, and a dispersion of modified casein in water, the native structure of the casein having been disrupted sufficiently to cause a composition to which the casein is added in use to gel.

2. A gelling agent according to claim 1 in which the plasticizer is glycerol.

3. A gelled product which includes a gelling agent as defined in claim 1.

4. A gelled product according to claim 3 which is a food product.

5. A gelled product according to claim 3 which is a delivery matrix which comprises (a) a matrix which includes the modified casein; and (b) an active agent incorporated in the matrix.

6. A gelled product according to claim 5 wherein the active agent is a pharmaceutical, insect or animal attractant or repellant.

7. A method of preparing a gelling agent which comprises the steps of:

(a) forming a dispersion comprising a plasticizer, casein and water;

(b) heating the dispersion for a sufficient time and to a sufficient temperature to disrupt the native structure of the casein.

8. A method according to claim 7 in which the dispersion is heated to a temperature of 95° C. or above.

9. A method according to claim 8 in which the dispersion is heated to a temperature of at least 100° C.

10. A method according to claim 8 in which the dispersion is heated to a temperature of at least 110° C.

11. A method according to claim 10 in which the dispersion is maintained at a temperature of at least 110° C. for at least 5 minutes.

12. A modified casein gelling agent which is obtainable by a method as claimed in claim 7.

13. A modified casein gelling agent which is obtained by a method as claimed in claim 7.

14. A process of preparing a gelled product which comprises adding a gelling agent comprising a plasticizer, and a dispersion of modified casein in water, the native structure of the casein having been disrupted sufficiently to cause a composition to which the casein is added in use to gel.

15. A process of preparing a gelled product which comprises using casein and a plasticizer as a gelling agent.

16. A method of preparing a gelled product which comprises the following steps:
   (a) forming a dispersion comprising a plasticizer, casein and water;
   (b) heating the dispersion for a sufficient time and to a sufficient temperature to disrupt the native structure of the casein; and
   (c) removing the source of heat, adding other gellable components and allowing the resulting mixture to set into a gel.

17. A method according to claim 16 wherein the dispersion also comprises a buffer to maintain the pH in the range of about 6.1 to about 10.1.

18. A method according to claim 16 wherein the dispersion is heated to temperature of at least 95° C.

19. A method according to claim 18 wherein the dispersion is heated to a temperature of at least 100° C.

20. A method according to claim 18 wherein the dispersion is heated to a temperature of at least 110° C.

21. A gelled product prepared by a method as claimed in claim 16.

22. A gelling agent consisting essentially of a plasticizer, and a dispersion of modified casein in water, the native structure of the casein having been disrupted sufficiently to cause a composition to which the casein is added in use to gel.

23. A gelling agent which comprises a plasticizer and a dispersion of modified casein in water, the native structure of the casein having been disrupted sufficiently to cause a composition to which the casein is added in use to gel, and wherein the amount of casein present is greater than 40% by weight of the plasticizer.

24. A meltable gelling agent which comprises a plasticizer and a dispersion of modified casein in water, the native structure of the casein having been disrupted sufficiently to cause a composition to which the casein is added in use to gel.

* * * * *

UNITED STATES PATENT AND TRADEMARK OFFICE
CERTIFICATE OF CORRECTION

PATENT NO.     : 6,610,348 B2
DATED          : August 26, 2003
INVENTOR(S)    : Beyer et al.

It is certified that error appears in the above-identified patent and that said Letters Patent is hereby corrected as shown below:

Title page,
Item [73], Assignee, please delete "Fonterra Tech Limited, Auckland (NZ)", and insert -- Fonterra Tech Limited, Auckland (NZ), and University of Otago, Dunedin (NZ) --.

Signed and Sealed this

Twenty-seventh Day of July, 2004

JON W. DUDAS
*Acting Director of the United States Patent and Trademark Office*